United States Patent
Nackaerts et al.

(10) Patent No.: US 10,384,001 B2
(45) Date of Patent: Aug. 20, 2019

(54) FLUID FLOW DEVICE

(71) Applicant: NXP B.V., Eindhoven (NL)

(72) Inventors: Axel Nackaerts, Haasrode (NL); Micha Benjamin Disselkoen, The Hague (NL)

(73) Assignee: NXP B.V., Eindhoven (NL)

( * ) Notice: Subject to any disclaimer, the term of this patent is extended or adjusted under 35 U.S.C. 154(b) by 215 days.

(21) Appl. No.: 15/408,105

(22) Filed: Jan. 17, 2017

(65) Prior Publication Data
US 2018/0200431 A1   Jul. 19, 2018

(51) Int. Cl.
| | |
|---|---|
| *A61M 5/168* | (2006.01) |
| *A61M 5/14* | (2006.01) |
| *G01F 13/00* | (2006.01) |
| *G01F 15/075* | (2006.01) |
| *G01F 22/02* | (2006.01) |
| *G01F 3/00* | (2006.01) |

(52) U.S. Cl.
CPC ...... *A61M 5/16804* (2013.01); *A61M 5/1411* (2013.01); *A61M 5/1414* (2013.01); *A61M 5/1684* (2013.01); *A61M 5/1689* (2013.01); *A61M 5/16881* (2013.01); *G01F 3/00* (2013.01); *G01F 13/006* (2013.01); *G01F 15/0755* (2013.01); *G01F 22/02* (2013.01); *A61M 2205/18* (2013.01); *A61M 2205/3331* (2013.01); *A61M 2205/3576* (2013.01); *A61M 2205/50* (2013.01)

(58) Field of Classification Search
CPC .............. A61M 5/1689; A61M 5/1682; A61M 5/16804; A61M 5/16813; A61M 5/162; A61M 5/168; A61M 5/1411; A61M 5/1414; A61M 5/1684; A61M 5/16881; A61M 5/1412; A61M 5/40; A61M 2205/3379; A61M 2205/3306; A61M 2205/3331
See application file for complete search history.

(56) References Cited

U.S. PATENT DOCUMENTS

| | | | |
|---|---|---|---|
| 3,593,579 A | | 7/1971 | Kenmore et al. |
| 3,609,379 A | * | 9/1971 | Hildebrandt ........ A61M 5/1689 128/DIG. 13 |

(Continued)

FOREIGN PATENT DOCUMENTS

| | | |
|---|---|---|
| DE | 10 2014 107 599 B3 | 11/2015 |
| EP | 1 777 447 A2 | 4/2007 |

(Continued)

OTHER PUBLICATIONS

Shepherd, C.M.; "Design of Primary and Secondary Cells—II. An Equation Describing Battery Discharge"; Journal of the Electrochemical Society, vol. 112, Issue 7; 8 pages (1965).

(Continued)

*Primary Examiner* — Emily L Schmidt
*Assistant Examiner* — Nicholas J Chidiac

(57) ABSTRACT

One example discloses a fluid flow device, including: a drop chamber, having an interior, a fluid input, and a fluid output; a drop detector coupled to the drop chamber and configured to detect a fluid drop at the fluid input; a pressure sensor configured to monitor a pressure in the interior of the drop chamber; and a flow rate device configured to determine a fluid flow rate based on a number of fluid drops detected over a time period, and the pressure in the interior of the drop chamber.

18 Claims, 12 Drawing Sheets

(56) References Cited

U.S. PATENT DOCUMENTS

| | | | | |
|---|---|---|---|---|
| 3,890,968 | A | * | 6/1975 | Pierce .................. A61M 5/1684 604/65 |
| 4,038,981 | A | * | 8/1977 | LeFevre ................ A61M 5/1411 128/DIG. 13 |
| 4,038,982 | A | * | 8/1977 | Burke .................. A61M 5/1689 128/DIG. 13 |
| 4,319,568 | A | * | 3/1982 | Tregoning ........ A61M 5/16809 222/255 |
| 4,391,598 | A | | 7/1983 | Thompson |
| 4,402,310 | A | * | 9/1983 | Kimura .............. A61B 1/00068 600/158 |
| 4,551,134 | A | * | 11/1985 | Slavik ............... A61M 5/16809 128/DIG. 13 |
| 4,588,396 | A | * | 5/1986 | Stroebel ................... A61M 5/14 604/244 |
| 4,724,405 | A | | 2/1988 | Matthies et al. |
| 4,740,198 | A | | 4/1988 | Theeuwes |
| 4,778,451 | A | | 10/1988 | Kamen |
| 4,857,048 | A | | 8/1989 | Simons et al. |
| 5,588,963 | A | * | 12/1996 | Roelofs ............... A61M 5/1689 604/65 |
| 7,137,964 | B2 | | 11/2006 | Flaherty |
| 8,777,894 | B2 | | 7/2014 | Butterfield et al. |
| 2010/0111837 | A1 | * | 5/2010 | Boyden ................ A61K 9/0019 424/1.11 |
| 2011/0064612 | A1 | | 3/2011 | Franzoni et al. |
| 2013/0083191 | A1 | | 4/2013 | Lowery et al. |
| 2015/0367070 | A1 | * | 12/2015 | Reaves ............. A61M 5/16854 604/506 |

FOREIGN PATENT DOCUMENTS

| | | |
|---|---|---|
| IN | 3238/CHE/2013 | 8/2013 |
| WO | WO-93/09407 | 5/1993 |

OTHER PUBLICATIONS

Tremblay, Olivier et al; "Experimental Validation of a Battery Dynamic Model for EV Applications"; World Electric Vehicle Journal vol. 3; Stavanger, Norway; 10 pages (May 2009).

* cited by examiner

FLUID FLOW DEVICE

The present specification relates to systems, methods, apparatuses, devices, articles of manufacture and instructions for a fluid flow device.

SUMMARY

According to an example embodiment, a fluid flow device, comprising: a drop chamber, having an interior, a fluid input, and a fluid output; a drop detector coupled to the drop chamber and configured to detect a fluid drop at the fluid input; a pressure sensor configured to monitor a pressure in the interior of the drop chamber; and a flow rate device configured to determine a fluid flow rate based on a number of fluid drops detected over a time period, and the pressure in the interior of the drop chamber.

In another example embodiment, a flow control device coupled to the drop chamber and configured to increase or decrease the number of fluid drops detected over a time period in response to a signal from the flow rate device.

In another example embodiment, the drop detector is a capacitive sensor.

In another example embodiment, a fluid reservoir is coupled and configured to supply a fluid to the fluid input of the drop chamber; and the fluid flow rate is a function of a hydrostatic pressure generated by a fluid in the fluid reservoir.

In another example embodiment, the flow rate device includes a computing unit configured to track or control the fluid flow rate over time.

In another example embodiment, the computing unit is configured to generate an alarm in response to at least one of: a fault condition, a minimum fluid supply, a fluid reservoir empty, a minimum fluid flow rate, or a maximum fluid flow rate.

In another example embodiment, the flow control device is positioned at either the fluid input or the fluid output.

In another example embodiment, the number of fluid drops detected over the time period is increased or decreased by opening or closing a valve.

In another example embodiment, the valve is configured to move between a closed position and an open position in response to a magnetic field.

In another example embodiment, the valve is within the interior of the drop chamber.

In another example embodiment, the valve includes a first set of magnets, and the device further comprises a second set of magnets outside of the drop chamber, wherein the valve is configured to move between a closed and a open positions based on a position of the second set of magnets and the first set of magnets.

In another example embodiment, the second set of magnets surround an exterior surface of the drop chamber.

In another example embodiment, the second set of magnets are moved with a servo motor or a linear motor.

In another example embodiment, the servo or linear motor include frictional elements configured to maintain a current valve position when the servo or linear motor are in a quiescent state.

In another example embodiment, the flow rate device includes a communications unit configured to control the flow control device in response to wireless signals.

In another example embodiment, the fluid flow device is configured as an intravenous therapy device.

According to an example embodiment, an article of manufacture including at least one non-transitory, tangible machine readable storage medium containing executable machine instructions for fluid flow: wherein the article includes: a drop chamber, having an interior, a fluid input, and a fluid output; a drop detector coupled to the drop chamber and configured to detect a fluid drop at the fluid input; a pressure sensor configured to monitor a pressure in the interior of the drop chamber; and a flow rate device configured to determine a fluid flow rate based on a number of fluid drops detected over a time period, and the pressure in the interior of the drop chamber; and a flow control device coupled to the drop chamber and configured to increase or decrease the number of fluid drops detected over a time period in response to a signal from the flow rate device; and a fluid reservoir coupled and configured to supply a fluid to the fluid input of the drop chamber; and wherein the instructions include: calculate a fluid fill level of the fluid reservoir; set the flow control device to an initial opening state; count a current number of fluid drops entering the drop chamber using the drop detector; convert the current number of fluid drops into a current flow rate based on the pressure monitored by the pressure sensor; if the current flow rate is different from a desired flow rate, then adjust the flow control device to a next opening state.

In another example embodiment, the instructions further comprise: generating an alarm in response to at least one of: a fault condition, a minimum fluid level in the fluid reservoir, an empty fluid reservoir, a minimum fluid flow rate, or a maximum fluid flow rate.

In another example embodiment, the instruction for calculating the fluid fill level further comprises: setting the flow control device to a closed state; and measuring the drop chamber pressure with the pressure sensor to recheck the fluid fill level of the fluid reservoir.

The above discussion is not intended to represent every example embodiment or every implementation within the scope of the current or future Claim sets. The Figures and Detailed Description that follow also exemplify various example embodiments.

Various example embodiments may be more completely understood in consideration of the following Detailed Description in connection with the accompanying Drawings, in which:

Figure 1:
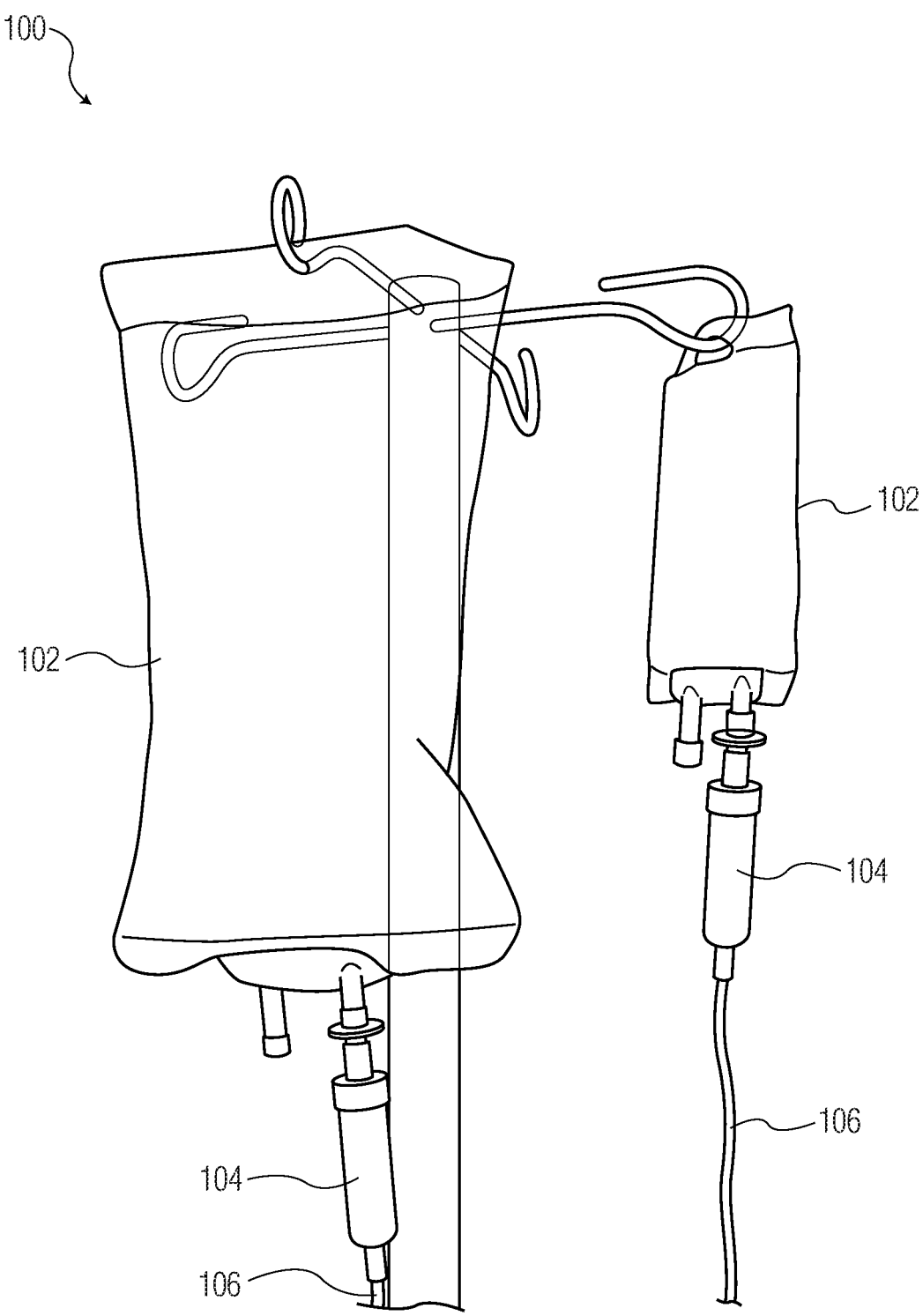
FIG. 1 is an example intravenous therapy apparatus.

While the disclosure is amenable to various modifications and alternative forms, specifics thereof have been shown by way of example in the drawings and will be described in detail. It should be understood, however, that other embodiments, beyond the particular embodiments described, are possible as well. All modifications, equivalents, and alternative embodiments falling within the spirit and scope of the appended claims are covered as well.

DETAILED DESCRIPTION

Fluid flow is important in a variety of device, apparatus, system and method domains. For example, flow monitoring and control in intravenous therapy is critical to successful patient outcomes.

FIG. 1 is an example intravenous (IV) therapy apparatus 100. This apparatus 100 is for dispensing fluids directly into the bloodstream of a patient. The apparatus 100 includes an IV therapy bag 102 and a drop chamber 104. The bag 102, drop chamber 104, and tubing 106 permit fluid to flow into a vein of the patient.

Drops form in the drop chamber 104 by a combination of hydrostatic pressure in the bag 102 and tubing between the bag 102 and drop chamber 104, and fluid resistive forces, such as from capillary forces, and counter-pressure from a drop regulator (not shown).

The drop regulator (not shown) can be a mechanical pressure clamp which, in response to a user's manual movement, regulates fluid flow through the tube 106. The drop rate, however, varies over time as the hydrostatic pressure of the fluid from the bag 102 changes. Since manual intervention is required to correct this variation, drop rate and drop size are not well controlled.

In another example (not shown) fluid flow can be controlled by an infusion pump (e.g. drop pump). Such pumps however are quite expensive (e.g. over $1,000 each).

Manually setting the flow rates in either of the these two examples is also be time-consuming for a caregiver (e.g. Doctor, Nurse, etc.).

Now presented is a fluid flow device, which in some embodiments can be priced at under $10 each. The fluid flow device can be a disposable single-use device for enhanced sterility in a medical or lab setting. In other embodiments, the lower price of the fluid flow device, places it within economic reach of customers not able to afford a more expensive flow control device, but who still require fluid flow device with high accuracy and remote control.

The fluid flow device discussed below, monitors a fluid drop rate and drop size (e.g. $1/20^{th}$ of a milliliter) by capacitive sensing and pressure monitoring. A flow control device (e.g. actuator) can be configured to actively control the flow/drop rate based on the monitoring results. In one embodiment, the fluid flow device is configured to be wirelessly controlled over a wireless communication channel (e.g. NFC, NFMI, etc.).

A computing unit (e.g. firmware, a state machine, and/or software) performs fluid flow calculations based on the monitoring results and the entire device can be powered by a battery. Instructions within the computing unit enable drop rate measurements and fluid volume calculations to be tracked over time.

The computing unit can be designed to generate automatic alarms based on selected fault conditions such as: when a fluid supply bottle is empty, flow is halted perhaps due to a blocked tube, fluid flow not within tolerances perhaps because an unexpected liquid is passing through the fluid flow device.

The computing unit can also be designed to permit automatic local or remote control of drop rate over time (e.g. preprogrammed constant or variable rate) which can reduce an amount of time caregivers must spend monitoring and controlling the flow rate.

In one example embodiment, the fluid flow device is embedded with an IV drop chamber for regulating fluids supplied to a hospital patient.

Figure 2:
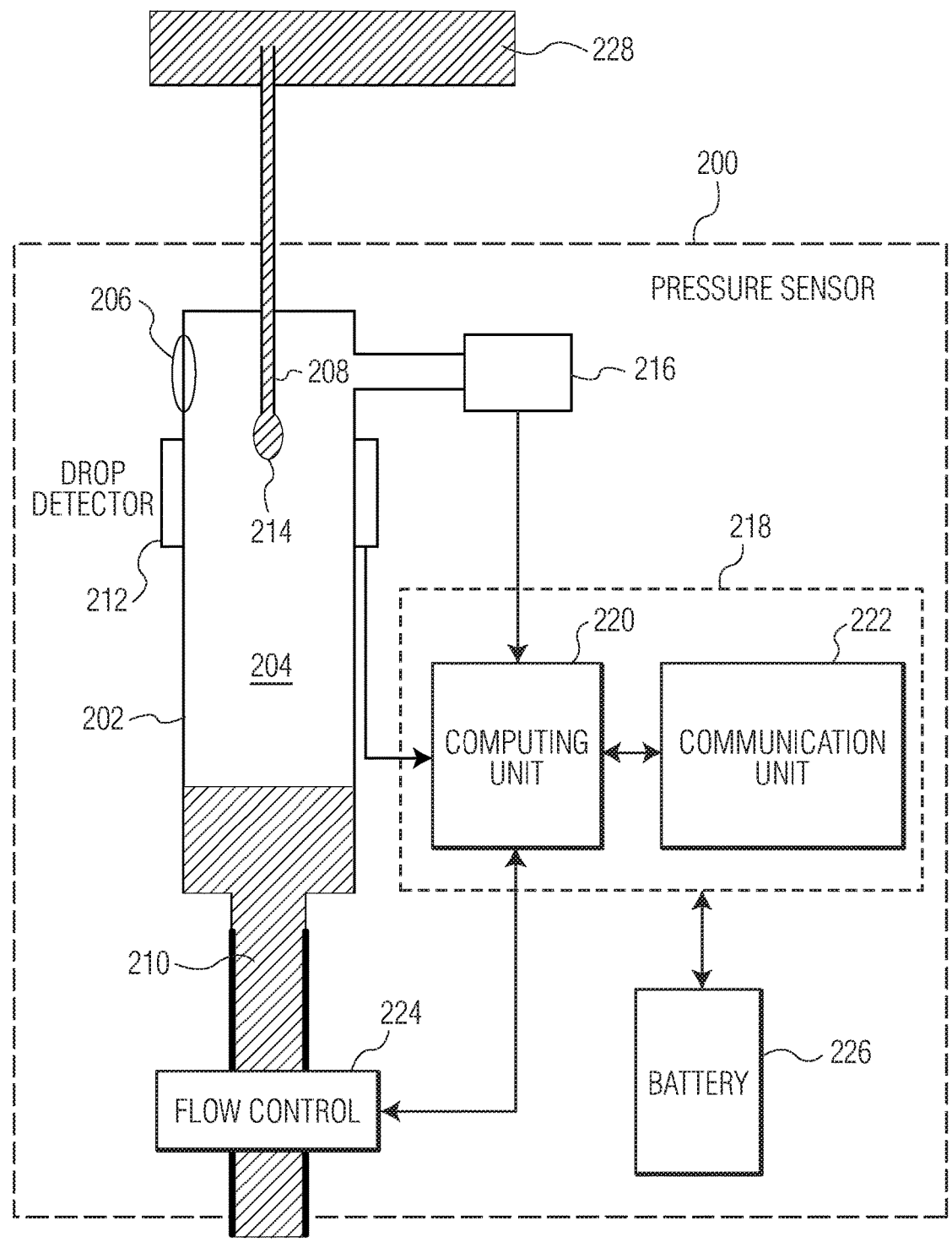
FIG. 2 is an example of a first fluid flow device.

FIG. 2 is an example of a first fluid flow device 200. The first fluid flow device 200 includes a drop chamber 202, a drop detector 212 (e.g. capacitive sensor), a pressure sensor 216, a flow rate device 218, a flow control device 224 (e.g. of a first type, external to the drop chamber 202) and a power supply 226. The drop chamber 202 includes an interior 204, an exterior surface 206, a fluid input 208, and a fluid output 210. The flow rate device 218 includes a computing unit 220 and a communications unit 222. When fluid is in a fluid reservoir 228 (e.g. bottle, bag, etc.), then a fluid drop 214 forms at the fluid input 208.

In one example embodiment the fluid flow device is configured as an intravenous therapy device.

The drop detector 212 is coupled to the drop chamber 202 and configured to detect the fluid drop 214 at the fluid input 208. In one example embodiment, the drop detector 212 is a capacitive sensor.

The pressure sensor 216 is configured to monitor a pressure in the interior 204 of the drop chamber 202.

The flow rate device 218 is configured to determine a fluid flow rate based on a number of fluid drops detected over a time period, and the pressure in the interior 204 of the drop chamber 202. The flow rate device 218 in one example embodiment, includes the communications unit 222 configured to control the flow control device 224 in response to wireless signals, such as NFC or NFMI.

As the drop grows in the drop chamber 202, drop detector 212 will measure a capacitance change and the pressure sensor 216 will measure a pressure and due to a volume of air being replaced by fluid. Since volume of air being replaced by fluid is related to the volume of the drop, the flow rate device 218 calculates the fluid flow rate by monitoring pressure and capacitance over time.

Additional discussion on how the flow rate device 218 calculates the fluid flow rate by monitoring pressure and capacitance is now presented.

Working principle as a fluid reservoir 228 level sensor. In a static no flow condition, the drop chamber 202 is pressurized by the liquid present in the reservoir 228. The principle behind this raise of pressure is that at a certain depth in a fluid the pressure is:

$$P_{fluid} = \rho g h \qquad (3\text{-}3)$$

where:
ρ=density of liquid
g=gravitational acceleration
h=fluid height above point Translating this principle into the first fluid flow device 200 of FIG. 2, a difference in pressure of the space inside the drop chamber 202 and atmospheric pressure is related to the height of the water column above the drop forming orifice (i.e. at the point of the fluid drop 214). Therefore measuring the pressure inside the drop chamber 202 gives an indication of the fluid height in the reservoir 228 above the outlet.

Although fluid height is not volume, the parameter is still of interest: The actual shape of the reservoir 228 determines the relation between volume and measured pressure/fluid height. The volume inside the reservoir 228 is not necessarily linearly related to the pressure measured in the drop chamber 202.

To be able to estimate the actual volume in the reservoir 228 a certain "pressure profile" has to be made. This profile can then be adjusted with the two main boundary conditions of the system: First, an initial liquid volume & measured pressure of reservoir 228 when full and, Second, by recording the pressure inside the drop chamber 202 when the reservoir 228 is empty. Both boundary conditions are known throughout the use of the system.

The pressure sensor 216 measures the pressure inside the drop chamber 202 and transfer this pressure information to the flow rate device 218. In one example, only a top ⅔ of the drop chamber 202 is filled with air. This air region is thus one of the preferred locations for the pressure sensor 216. It is possible to place the pressure sensor 216 either inside the drop chamber 202, or outside the drop chamber 202 and connect it through the wall of the drop chamber 202.

In case the pressure sensor 216 is placed inside the drop chamber 202 an absolute pressure sensor is required and if the pressure sensor 216 is placed outside of the drop chamber 202 either a differential or absolute pressure sensor can be used.

As placement of the pressure sensor 216 inside the drop chamber 202 is more complicated to realize, might bring contamination or sterility issues, and has no practical advantage, an externally connected sensor is implemented. This pressure sensor 216 is connected through the wall with the upper part of the drop chamber 202 at the round edge above the outlet of the drop forming orifice. This place can be used because it reduces the probability of water getting into the tube connecting the sensor.

In one example embodiment, an expected pressure difference between a full and empty reservoir 228 is from 103778 Pascals to 101325 Pascals of pressure.

In another example embodiment, a physical design of the drop chamber 202 fluid input 208 sets a drop size for a given fluid at a given drop chamber 202 pressure. Given such a drop size, the drop detector 212 capacitance measurement can alternately be used just as a "counter" and the flow rate device 218 can use the drop count value, the pressure sensor 216 pressure, and the known physical characteristics of the drop chamber 202 to calculate the fluid flow rate.

The fluid reservoir 228 is coupled and configured to supply a fluid to the fluid input 208 of the drop chamber 202, and the fluid flow rate is a function of a hydrostatic pressure generated by a fluid in the fluid reservoir 228.

The flow control device 224 is coupled to the drop chamber 202 and configured to increase or decrease the number of fluid drops detected over a time period in response to a signal from the flow rate device 218. The flow control device 224 can be positioned at either the fluid input 208 or the fluid output 210.

The flow control device 224 (e.g. a servo actuator) allows a counter-pressure in the drop chamber 202 to be actively changed. This counter-pressure modulates the flow of fluid exiting the drop chamber 202. Thus under the control of the flow rate device 218, a constant fluid flow/drop rate can be maintained which is independent of the amount of fluid remaining in the fluid reservoir 228.

Thus when the flow control device 224 is fully closed, no drops can form and the hydrostatic pressure measured by the pressure sensor 216 can be used to calculate the amount of fluid remaining in the fluid reservoir 228.

In some example embodiments, the flow rate device 218 includes the computing unit 220 configured to track or control the fluid flow rate over time. The computing unit 220 can be a set of discrete circuit elements, logic blocks, firmware or software running on a microcontroller or microprocessor.

Using instructions logically coded or programmed into the computing unit 220, the fluid flow rate can have a complex flow profile over time. For example, a patient's intravenous therapy could begin with a slowly increasing flow rate over 10 minutes, so as not to shock the patient.

In one example embodiment, the computing unit 220 is configure to generate an alarm in response to at least one of: a fault condition, a minimum fluid supply, a fluid reservoir 228 empty, a minimum fluid flow rate, or a maximum fluid flow rate.

Fault conditions may include: an empty bottle or bag; an obstruction in the downline tubing (e.g. flow too low for a given bag volume and flow control device 224 valve position); a leak in the downline tubing (e.g. flow too high for a given bag volume and flow control device 224 valve position); air leaks in the system (e.g. pressure dropping too fast). In such fault conditions, a buzzer, display or LED can be added to the fluid flow device 200 to warn the caregiver of the error conditions, or communications though the communications unit 222 (e.g. long-range radio, Bluetooth which is a wireless communications protocol with short-wavelength UHF radio waves with frequency from 2.400 to 2.485 Ghz, a hospital system link, etc.) can remotely warn a hospital's staff.

In one example embodiment, the communications unit 222 includes a smart NFC tag. Then a second smart tag is attached to the fluid reservoir 228 (e.g. bottle, bag, etc.) and contains a patent's prescription (e.g. X ml/minute flow). A caregiver scans the fluid reservoir 228 with a smartphone and a specific application. The caregiver then scans the patient's identification, and touches the NFC tag of the IV apparatus to activate it and transfer the prescription to the computing unit 220. The computing unit 220 can also be programmed to check a validity of the prescription-patient pairing.

Figure 3:
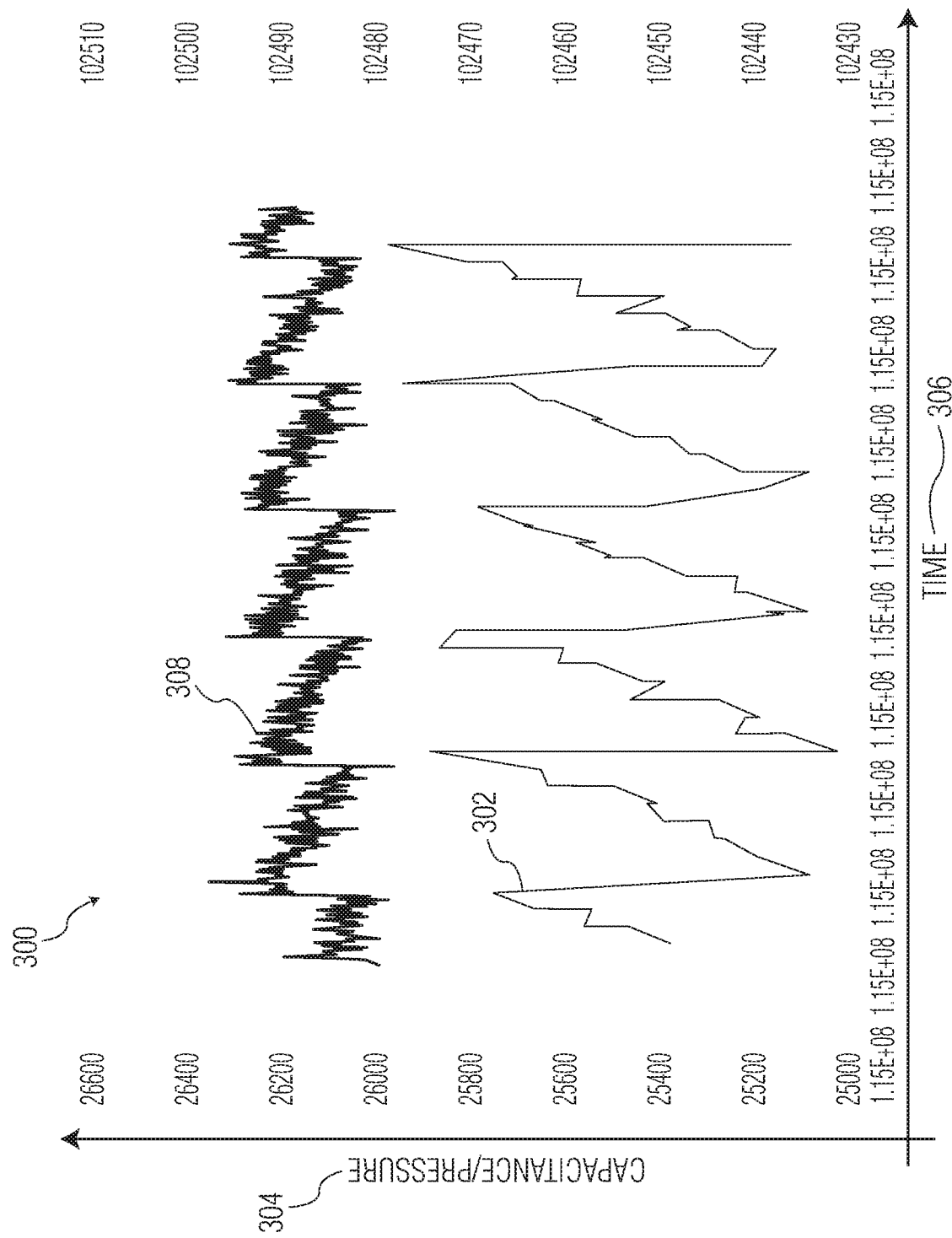
FIG. 3 is an example first set of fluid flow measurements.

FIG. 3 is an example first set of fluid flow measurements 300. A first waveform 302 shows the pressure sensor 216 pressure 304 verses time 306. High pressure corresponds to a maximum drop size. Low pressure corresponds to a minimum drop size. The increase in pressure in the FIG. 3 corresponds to a growth in formation of one drop and the sharp drop in pressure corresponds to the drop falling from the drop chamber fluid input orifice, thereby creating a "saw-tooth" pressure sensor value pattern.

A second waveform 308 shows the drop detector 212 capacitance 304 over time 306. High capacitance corresponds to a minimum drop size. Low capacitance corresponds to a maximum drop size. Different liquids will have different capacitance characteristics, based upon the dielectric properties of the fluid passing through the drop chamber.

Both the first waveform 302 and the second waveform 308 can also vary depending upon a temperature of the fluid.

Figure 4:
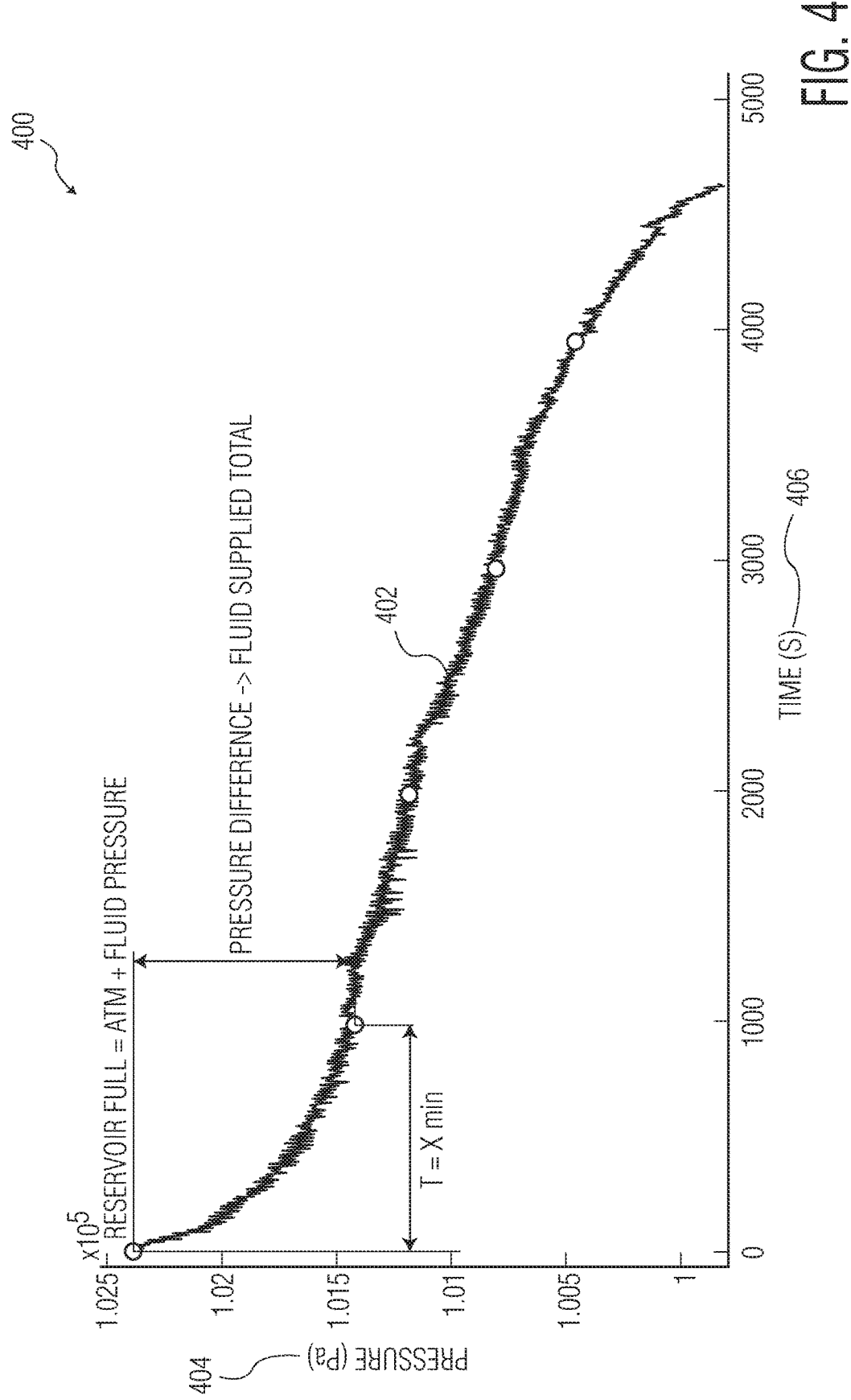
FIG. 4 is an example second set of fluid flow measurements.

FIG. 4 is an example second set of fluid flow measurements 400. A first waveform 402 shows drop chamber pressure 404 verses time 406 as fluid flows out of the reservoir 228. Such data could be programmed into the computing unit 222.

In one example embodiment, a formula for calculating the fluid flow rate from the drops counted is "fluid flow rate"= ((drop volume)*drops counted)/(counting time window).

Note that the pressure measured is not only influenced by the water column in the reservoir 228. A pressure drop due to tubing resistance and the outflow will influence the measurement as well. If the flow rate is low, such frictional losses are treated as constant offsets by the flow rate device 218.

FIG. 4 shows that the pressure during emptying is not linear. The first waveform 402 can be split up into three stages: first, a nonlinear reducing decrease rate; second, a stable linear decrease rate; and third, a nonlinear growing decrease rate.

This profile is a result of the shape and material of the reservoir 228. For example, if the reservoir 228 is a plastic IV bag, then during the first stage the bag is completely filled with liquid. The plastic material of the bag is stretched and pressures the liquid initially. As the bag is emptying it becomes relaxed, in the second stage the liquid flows out by atmospheric pressure and mass. During this stage the bag deforms easily and has minimal influence. In the third (last) stage, pressure reduces at an increasing rate. When the shape of the bag is analyzed it can be seen that the width of the reservoir 228 reduces in the bottom part. When outflow is kept constant, the water column height (and thus the measured pressure) in the center will decrease at an increasing rate.

Figure 5A:
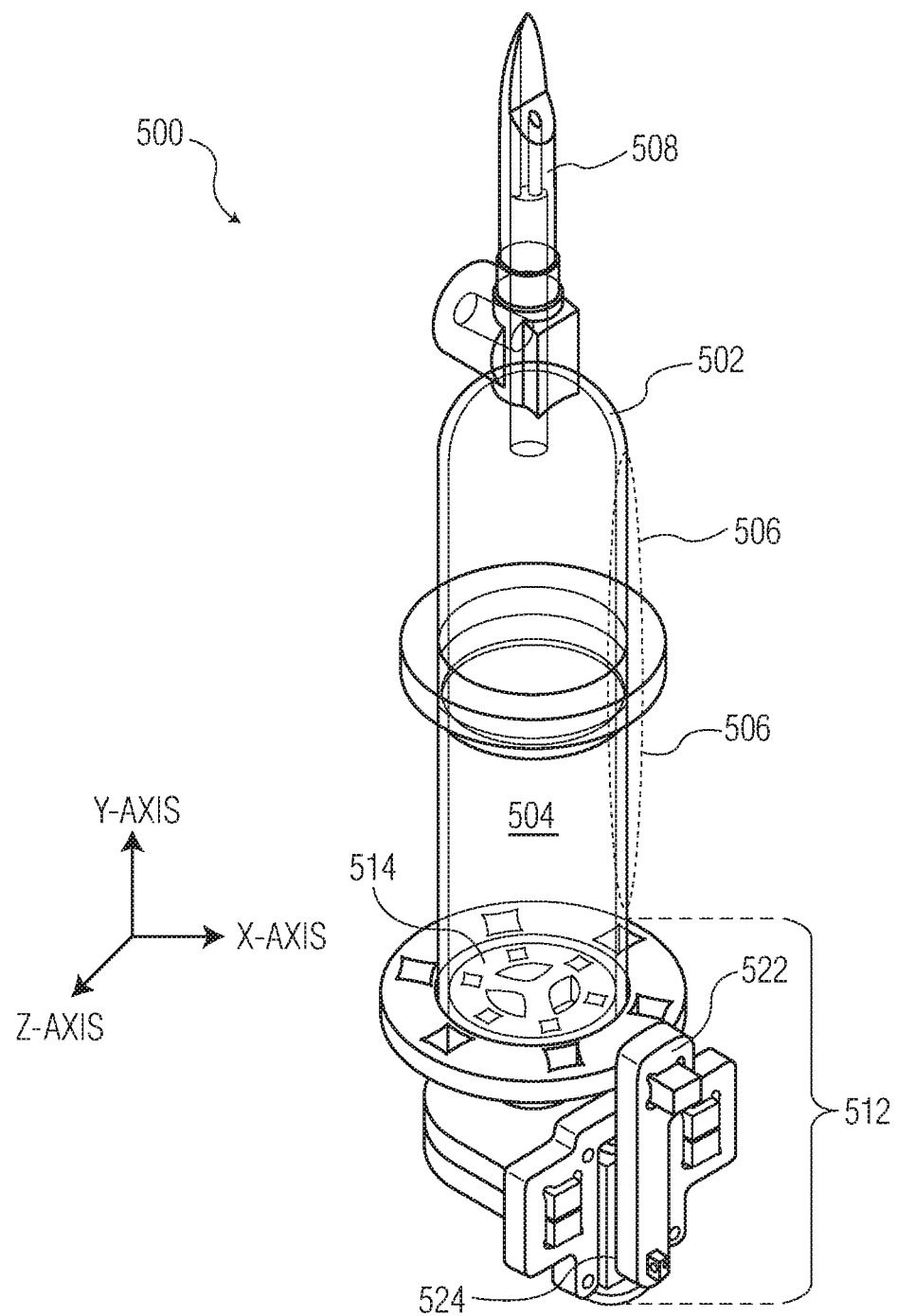
FIG. 5A is an example perspective view of a second fluid flow control device.
Figure 5B:
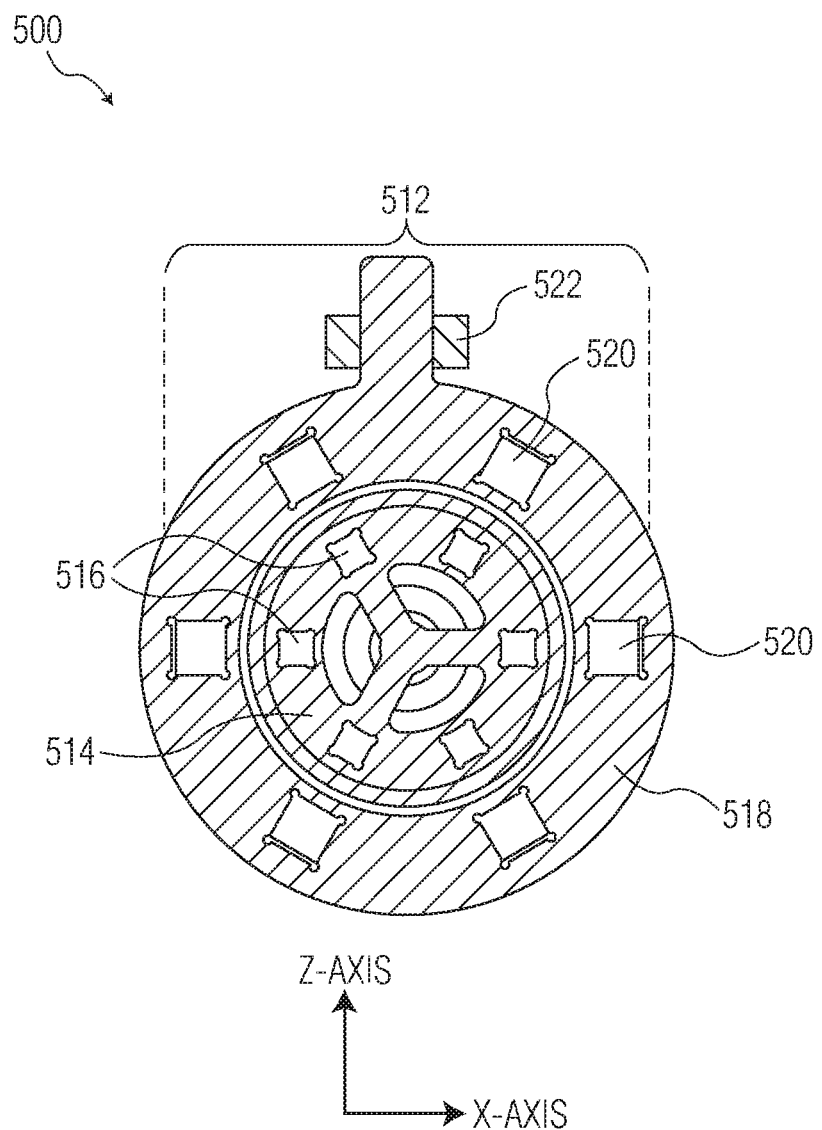
FIG. 5B is an example first cross-sectional view of the second fluid flow control device.

FIG. 5A is an example perspective view of a second fluid flow control device 500. FIG. 5B is an example first cross-sectional view of the second fluid flow control device 500.

The second fluid flow device 500 includes: a drop chamber 502, a drop detector (not shown), a pressure sensor (not shown), a flow rate device (not shown), and a flow control device 512 (e.g. of a second type, internal to the drop chamber 502).

The drop chamber 502 includes: an interior 504, an exterior surface 506, a fluid input 508, and a fluid output 510.

The flow rate device (not shown) includes: a computing unit (not shown), and a communications unit (not shown).

The flow control device 512 includes: an inner ring 514, an inner ring magnets 516, a valve (e.g. needle type) (not shown), an outer ring 518, an outer ring magnets 520, an outer ring servo control arm 522, and an outer ring servo linear motor 524.

The number of fluid drops detected by the drop detector over a time period is increased or decreased by opening or closing a valve (e.g. needle valve, plunger, etc.) inside of the drop chamber 502. See valve 602 in FIGS. 6A and 6B for an example of the valve. Note that the first fluid flow device 200 embodiment (see FIG. 2) positioned the flow control device 224 in the tubing outside of the drop chamber 202.

The valve is configured to move between a closed position and an open position in response to a magnetic field within the interior 204 of the drop chamber 202.

The valve includes a first set of magnets (e.g. inner ring magnets 516) within the inner ring 514. The second set of magnets (e.g. outer ring magnets 520) are within the outer ring 518 outside of the drop chamber 202. The valve is configured to move between the closed and the open positions based on a position of the second set of magnets and the first set of magnets.

In one example embodiment the inner ring magnets 516 and outer ring magnets 520 have opposing magnetic polarizations. However a geometric configuration, strength and polarity of the magnets 516, 520 may be chosen such that no motor-like rotation occurs and that optimal link of valve controlling force is achieved. The magnetic link should be stronger than the expected frictional forces between inner ring 514 and an inside surface of the drop chamber 502.

In this example, the outer ring magnets 520 surround the exterior surface 506 of the drop chamber 202. Other magnetic arrangements are possible. The outer ring magnets 520 are moved with the servo motor or a linear motor 504 using the outer ring servo control arm 522.

In one example, the servo or linear motor 504 includes frictional elements configured to maintain a current valve position when the servo or linear motor 504 is in a quiescent state.

The inner ring 514 and valve can be sterilized by conventional methods (e.g. heat, chemicals, gamma rays) and made of medical-grade materials. The outer ring 518 can be clipped onto the drop chamber 502.

Figure 6A:
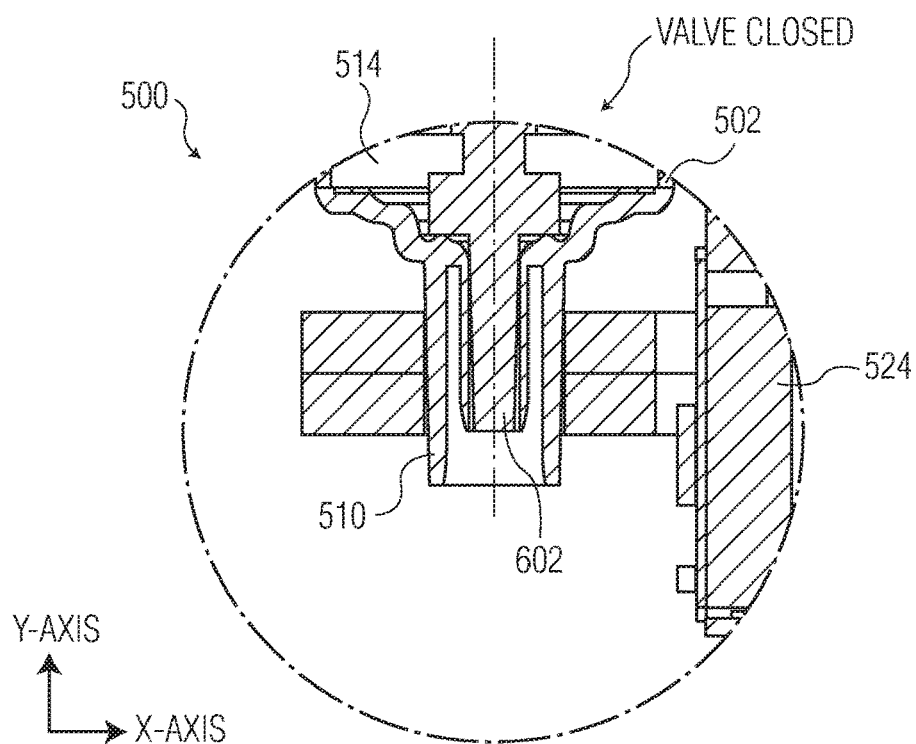
FIG. 6A is an example second cross-sectional view of the second fluid flow control device with a flow valve in a closed position.
Figure 6B:
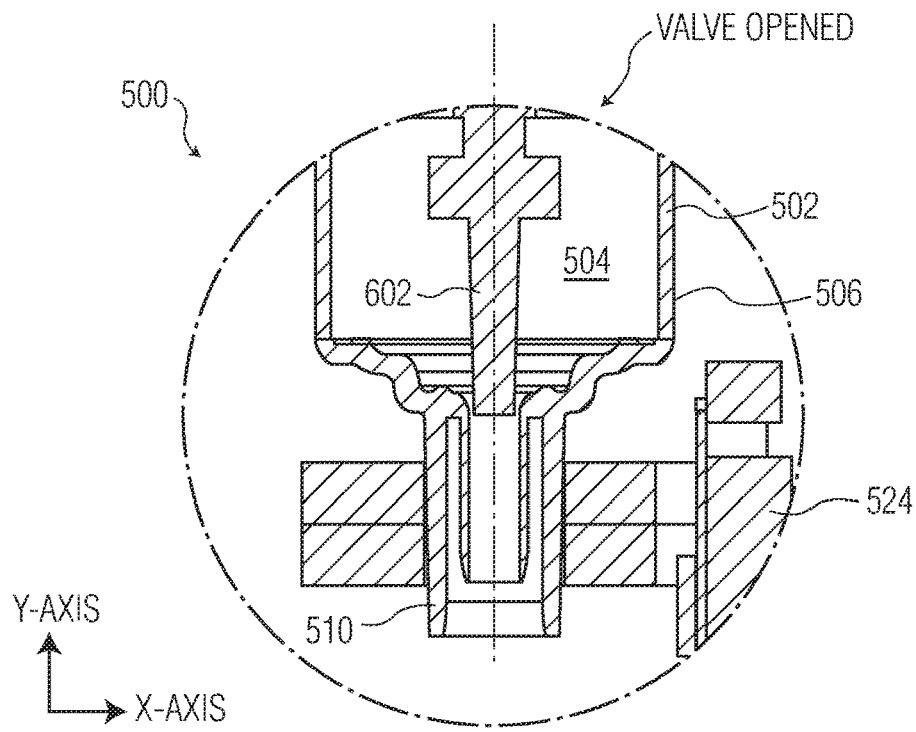
FIG. 6B is an example the second cross-sectional view of the second fluid flow control device with the flow valve in an open position.

FIG. 6A is an example second cross-sectional view of the second fluid flow control device 500 with a flow valve 602 in a closed position. FIG. 6B is an example the second cross-sectional view of the second fluid flow control device 500 with the flow valve 602 in an open position.

As can be seen, the shape of the valve 602 is substantially geometrically matched with the geometric shape of the fluid output 510 of the drop chamber. In one example embodiment, a length of the valve 602 is chosen such that sufficient pressure drop can be achieved to control the fluid flow rate.

When the valve is open, the pressure sensor (not shown) sees only a minimal pressure drop and fluid flows at a maximum rate dependent upon the hydrostatic pressure created by the level of fluid in the fluid reservoir (not shown). Intermediate valve 602 positions yield a variable pressure drop due to the properties of fluid flow in constricted spaces, which results in a reduction of flow depending on the position of the valve 602.

In some example embodiments, only a change in position of the valve 602 requires energy. A static position is kept otherwise due to frictional losses in a drivetrain of the outer ring servo linear motor 524 (e.g. in the gearbox). However, in an alternate embodiment the linear servo motor 524 is designed to return to a predetermined position when power is lost.

Figure 7A:
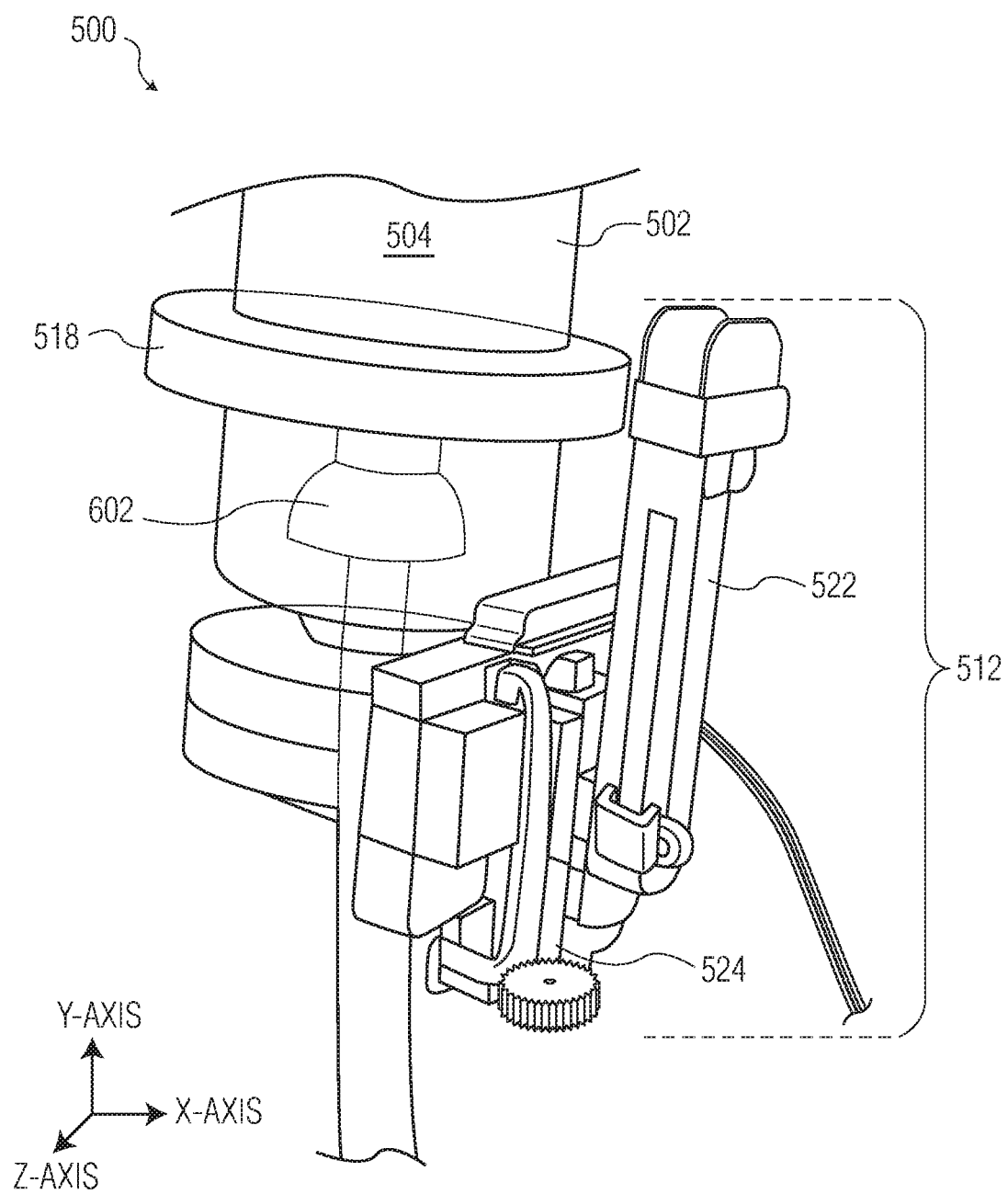
FIG. 7A is an example second perspective view of the second fluid flow control device with the flow valve in the closed position.
Figure 7B:
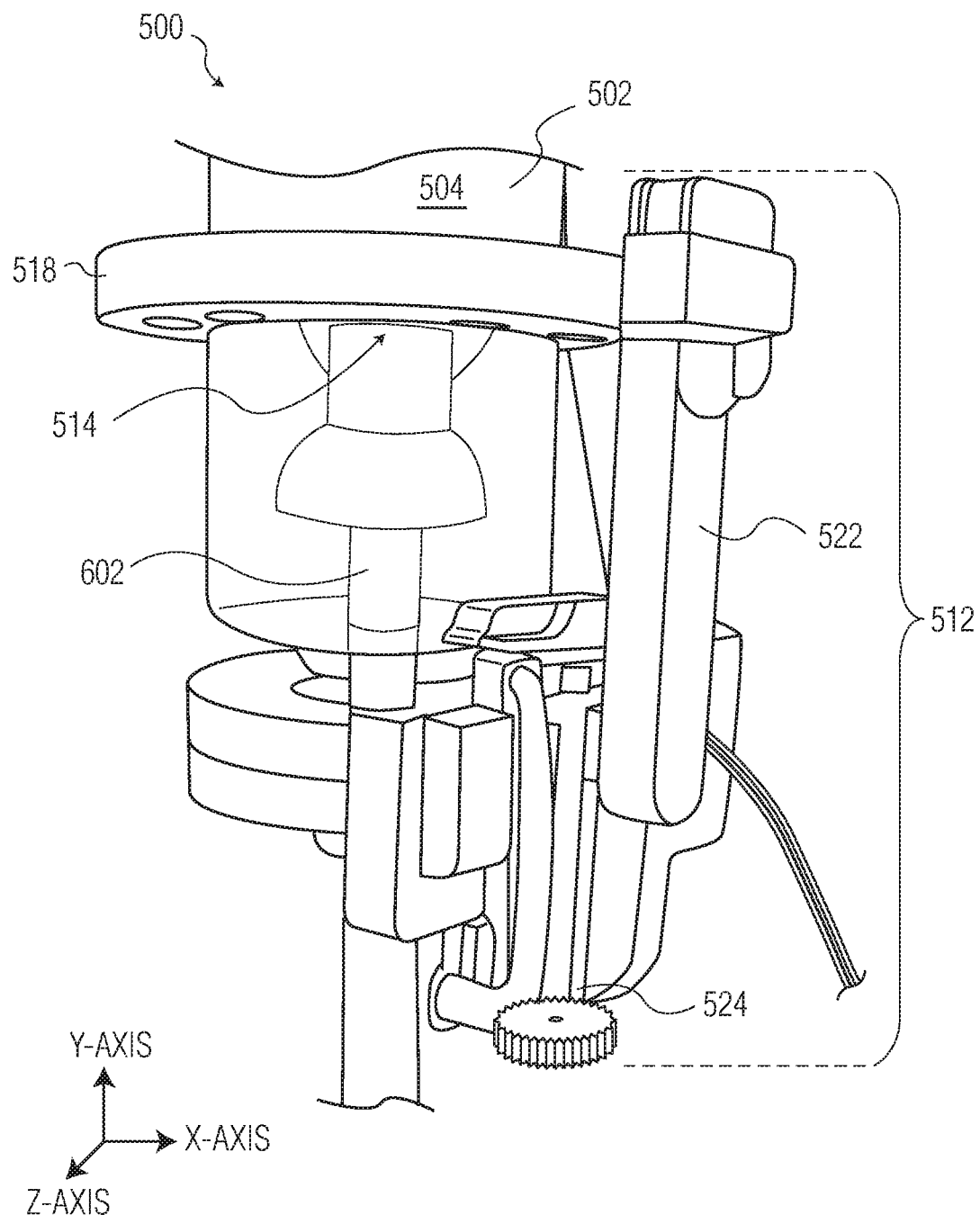
FIG. 7B is an example the second perspective view of the second fluid flow control device with the flow valve in the open position.

FIG. 7A is an example second perspective view of the second fluid flow control device 500 with the flow valve in the closed position. FIG. 7B is an example the second perspective view of the second fluid flow control device 500 with the flow valve in the open position.

In an alternate embodiment, the valve 602 design can be made such that a minimal flow is ensured in case the linear servo motor fails in a closed position. With both the flow rate monitoring and control by the flow rate device, variations in a valve shape and/or flow pressure drop can be accommodated.

Figure 8:
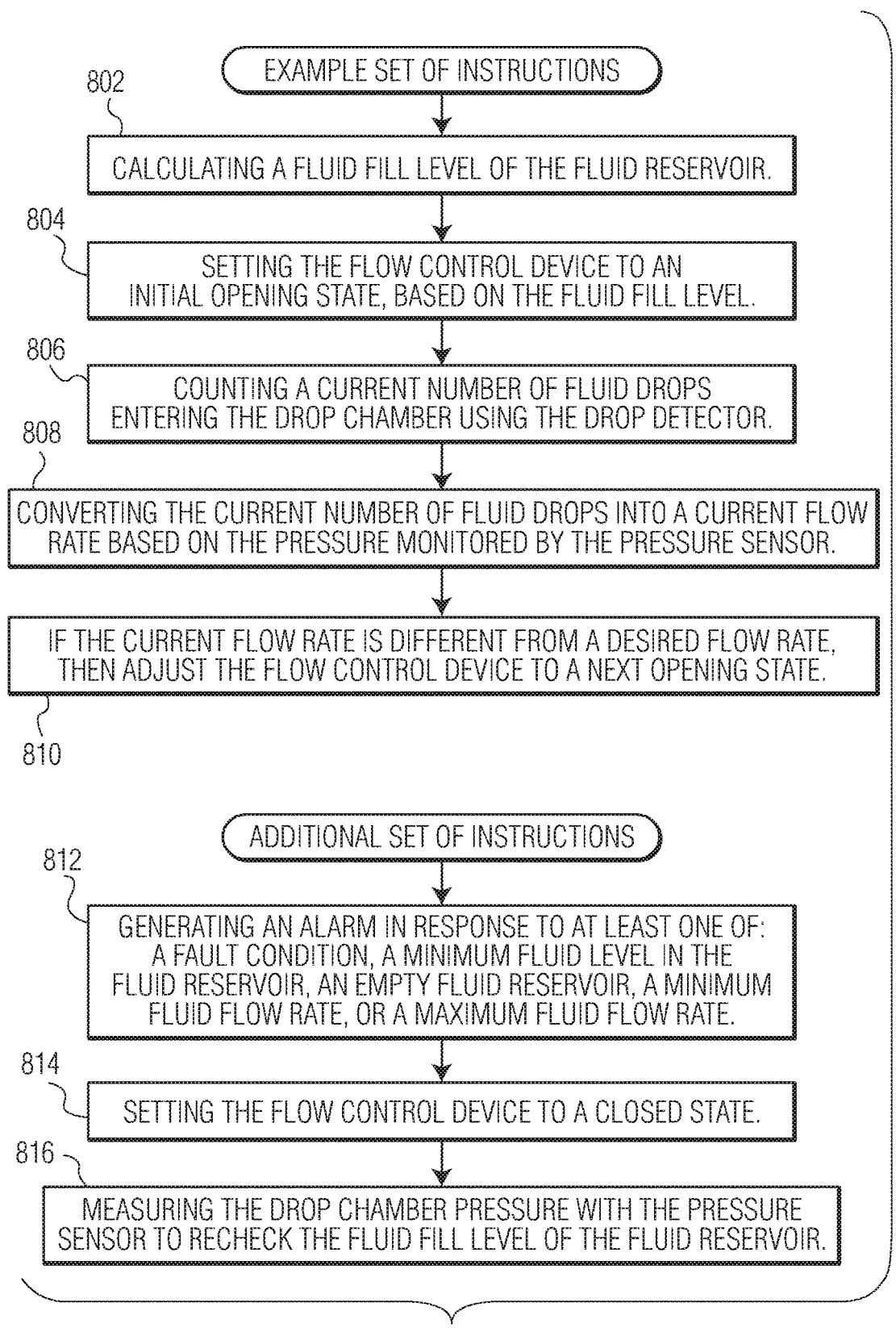
FIG. 8 is an example first set of instructions for enabling the first or second fluid flow devices.

FIG. 8 is an example first set of instructions 800 for enabling the first or second fluid flow devices. The order in which the instructions are discussed does not limit the order in which other example embodiments implement the instructions unless otherwise specifically stated. Additionally, in some embodiments the instructions are implemented concurrently.

The first example instruction set begins in 802, by calculating a fluid fill level of the fluid reservoir. Next in step 804 setting the flow control device to an initial opening state, based on the fluid fill level. Then in step 806, counting a current number of fluid drops entering the drop chamber using the drop detector. In step 808, converting the current number of fluid drops into a current flow rate based on the pressure monitored by the pressure sensor. In step 810, if the current flow rate is different from a desired flow rate, then adjust the flow control device to a next opening state.

The instructions can be augmented or replaced with one or more of the following additional instructions, presented in no particular order: 812—generating an alarm in response to at least one of: a fault condition, a minimum fluid level in the fluid reservoir, an empty fluid reservoir, a minimum fluid flow rate, or a maximum fluid flow rate; 814—setting the flow control device to a closed state; and 816—measuring the drop chamber pressure with the pressure sensor to recheck the fluid fill level of the fluid reservoir.

Figure 9:
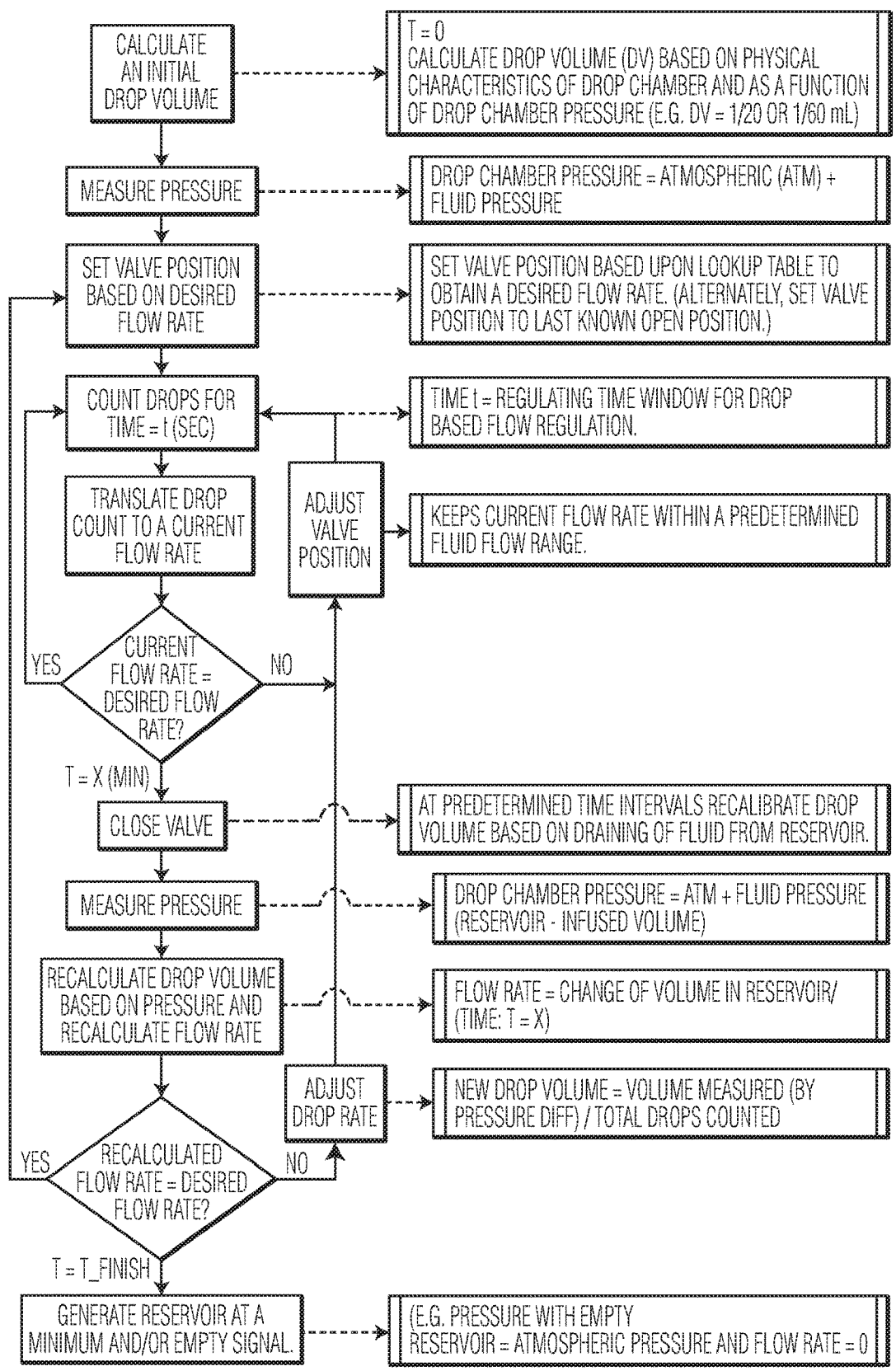
FIG. 9 is an example second set of instructions for enabling the first or second fluid flow devices.

FIG. 9 is an example second set of instructions 900 for enabling the first or second fluid flow devices.

Figure 10:
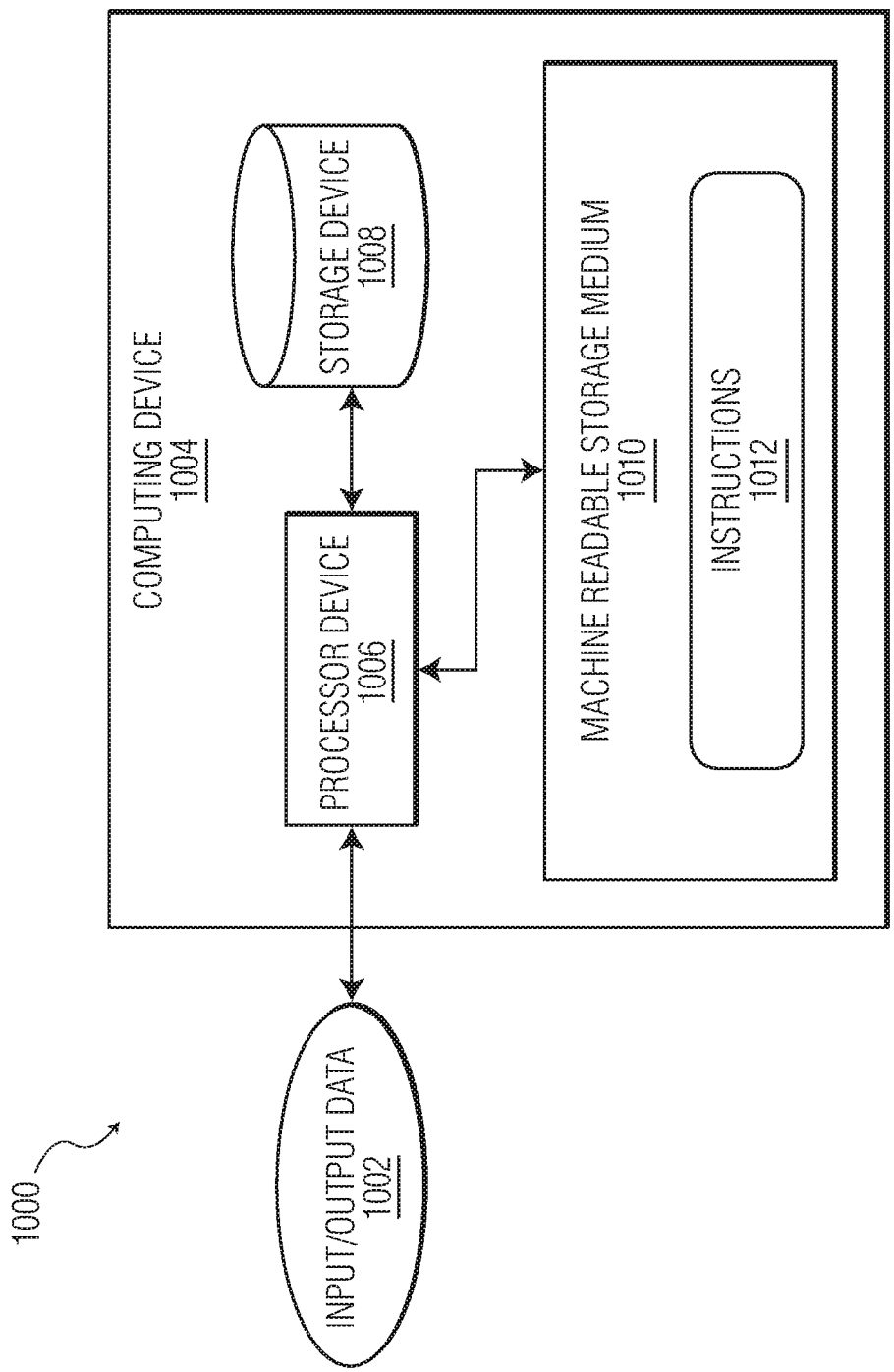
FIG. 10 is an example system for hosting instructions for enabling the first or second fluid flow devices.

FIG. 10 is an example system 1000 for hosting instructions for enabling the first or second fluid flow devices. The system 1000 shows an input/output data 1002 interface with an electronic apparatus 1004. The electronic apparatus 1004 includes a processor 1006, a storage device 1008, and a non-transient machine-readable storage medium 1010. The machine-readable storage medium 1010 includes instructions 1012 which control how the processor 1006 receives input data 1002 and transforms the input data into output data 1002, using data within the storage device 1008. Example instructions 1012 stored in the machine-readable storage medium 1010 are discussed elsewhere in this specification. The machine-readable storage medium in an alternate example embodiment is a non-transient computer-readable storage medium.

The processor (such as a central processing unit, CPU, microprocessor, application-specific integrated circuit (ASIC), etc.) controls the overall operation of the storage device (such as random access memory (RAM) for temporary data storage, read only memory (ROM) for permanent data storage, firmware, flash memory, external and internal hard-disk drives, and the like). The processor device communicates with the storage device and non-transient machine-readable storage medium using a bus and performs operations and tasks that implement one or more instructions stored in the machine-readable storage medium. The machine-readable storage medium in an alternate example embodiment is a computer-readable storage medium.

In some example embodiments the set of instructions described above are implemented as functional and software instructions. In other embodiments, the instructions can be implemented either using logic gates, application specific chips, firmware, as well as other hardware forms.

When the instructions are embodied as a set of executable instructions in a non-transient computer-readable or computer-usable media which are effected on a computer or machine programmed with and controlled by said executable instructions. Said instructions are loaded for execution on a processor (such as one or more CPUs). Said processor includes microprocessors, microcontrollers, processor modules or subsystems (including one or more microprocessors or microcontrollers), or other control or computing devices. A processor can refer to a single component or to plural components. Said computer-readable or computer-usable storage medium or media is (are) considered to be part of an article (or article of manufacture). An article or article of manufacture can refer to any manufactured single component or multiple components. The non-transient machine or computer-usable media or mediums as defined herein excludes signals, but such media or mediums may be capable of receiving and processing information from signals and/or other transient mediums.

In this specification, example embodiments have been presented in terms of a selected set of details. However, a person of ordinary skill in the art would understand that many other example embodiments may be practiced which include a different selected set of these details. It is intended that the following claims cover all possible example embodiments.

What is claimed is:

1. A fluid flow device, comprising:
a drop chamber, having an interior, a fluid input, and a fluid output;
a drop detector coupled to the drop chamber and configured to detect a fluid drop at the fluid input and to count the number of detected fluid drops in a counting time window;
a pressure sensor configured to monitor a pressure in the interior of the drop chamber; and
a flow rate device configured to determine a fluid flow rate based on a number of fluid drops detected over a time period, and the pressure in the interior of the drop chamber, wherein the fluid flow rate is calculated as ((drop volume)*drops counted)/(counting time window), where drop volume is a function of the monitored pressure and the drops counted and is calculated as drop volume=(volume of fluid measured by pressure differential)/(total drops counted between pressure measurements).

2. The device of claim 1:
wherein the drop detector is a capacitive sensor.

3. The device of claim 1:
further comprising a fluid reservoir coupled and configured to supply a fluid to the fluid input of the drop chamber; and
wherein the fluid flow rate is a function of a hydrostatic pressure generated by a fluid in the fluid reservoir.

4. The device of claim 1:
wherein the flow rate device includes a computing unit configured to track or control the fluid flow rate over time.

5. The device of claim 1:
wherein the computing unit is configured to generate an alarm in response to at least one of: a fault condition, a minimum fluid supply, a fluid reservoir empty, a minimum fluid flow rate, or a maximum fluid flow rate.

6. The device of claim 1:
wherein the flow rate device includes a communications unit configured to control the flow control device in response to wireless signals.

7. The device of claim 1:
wherein the fluid flow device is configured as an intravenous therapy device.

8. The device of claim 1, further comprising:
a flow control device coupled to the drop chamber and configured to increase or decrease the number of fluid drops detected over a time period in response to a signal from the flow rate device.

9. The device of claim 8:
wherein the flow control device is positioned at either the fluid input or the fluid output.

10. The device of claim 8:
wherein the number of fluid drops detected over the time period is increased or decreased by opening or closing a valve.

11. The device of claim 10:
wherein the valve is configured to move between a closed position and an open position in response to a magnetic field.

12. The device of claim 11:
wherein the valve is within the interior of the drop chamber.

13. The device of claim 12:
wherein the valve includes a first set of magnets;
further comprising a second set of magnets outside of the drop chamber;
wherein the valve is configured to move between a closed and an open positions based on a position of the second set of magnets and the first set of magnets.

14. The device of claim 13:
wherein the second set of magnets surround an exterior surface of the drop chamber.

15. The device of claim 14:
wherein the second set of magnets are moved with a servo motor or a linear motor.

16. An article of manufacture including at least one non-transitory, tangible machine readable storage medium containing executable machine instructions for fluid flow, comprising:
  a drop chamber, having an interior, a fluid input, and a fluid output;
  a drop detector coupled to the drop chamber and configured to detect a fluid drop at the fluid input and to count the number of detected fluid drops in a counting time window;
  a pressure sensor configured to monitor a pressure in the interior of the drop chamber; and
  a flow rate device configured to determine a fluid flow rate based on a number of fluid drops detected over a time period, and the pressure in the interior of the drop chamber, wherein the fluid flow rate is calculated as ((drop volume)*drops counted)/(counting time window), where drop volume is a function of the monitored pressure and the drops counted and is calculated as drop volume=(volume of fluid measured by pressure differential)/(total drops counted between pressure measurements); and
  a flow control device coupled to the drop chamber and configured to increase or decrease the number of fluid drops detected over a time period in response to a signal from the flow rate device; and
  a fluid reservoir coupled and configured to supply a fluid to the fluid input of the drop chamber; and
wherein the instructions include:
  calculate a fluid fill level of the fluid reservoir;
  set the flow control device to an initial opening state;
  count a current number of fluid drops entering the drop chamber using the drop detector;
  convert the current number of fluid drops into a current flow rate based on the pressure monitored by the pressure sensor, wherein the current flow rate is calculated as ((drop volume)*drops counted)/(counting time window), where drop volume is a function of the monitored pressure and the drops counted and is calculated as drop volume=(volume of fluid measured by pressure differential)/(total drops counted between pressure measurements);
  if the current flow rate is different from a desired flow rate, then adjust the flow control device to a next opening state.

17. The article of claim 16, wherein the instructions further comprise:
  generating an alarm in response to at least one of: a fault condition, a minimum fluid level in the fluid reservoir, an empty fluid reservoir, a minimum fluid flow rate, or a maximum fluid flow rate.

18. The article of claim 16, wherein the instruction for calculating the fluid fill level further comprises:
  setting the flow control device to a closed state; and
  measuring the drop chamber pressure with the pressure sensor to recheck the fluid fill level of the fluid reservoir.

* * * * *